United States Patent [19]
Verderber

[11] Patent Number: 5,385,468
[45] Date of Patent: Jan. 31, 1995

[54] REMOVABLE INSTRUMENT HOLDER

[75] Inventor: Gregory R. Verderber, Cincinnati, Ohio

[73] Assignee: Gregg Laboratories, Inc., Cincinnati, Ohio

[21] Appl. No.: 89,254

[22] Filed: Jul. 9, 1993

[51] Int. Cl.⁶ .............................................. A61C 1/02
[52] U.S. Cl. ............................................ 433/77; 433/77
[58] Field of Search ..................... 433/28, 33, 77, 78, 433/79, 49, 108

[56] References Cited

U.S. PATENT DOCUMENTS

| | | | |
|---|---|---|---|
| D. 336,131 | 6/1993 | Nordstrom et al. | D24/128 |
| 2,595,287 | 5/1952 | Perry | 362/226 |
| 3,702,940 | 11/1972 | Stewart | 433/28 |
| 3,904,841 | 9/1975 | Swatman | 433/28 |
| 4,330,281 | 5/1992 | Hayashi | 433/108 |
| 4,414,608 | 11/1983 | Furihata | 362/226 |
| 4,568,281 | 2/1986 | Hervey et al. | 433/30 |
| 5,127,830 | 7/1992 | Sheridan et al. | 433/77 |
| 5,139,421 | 8/1992 | Verderber | 433/30 |
| 5,161,970 | 11/1992 | Baskas | 433/77 |

Primary Examiner—Cary E. O'Connor
Attorney, Agent, or Firm—Jerrold J. Litzinger

[57] ABSTRACT

A holder assembly for a medical instrument having two sections releasably coupled together. One section is mounted to a support, while the second section, which contains a holder for a medical instrument, can be easily detached from the first section without the use of tools, such that the instrument holder may be sterilized along with the instrument.

15 Claims, 4 Drawing Sheets

REMOVABLE INSTRUMENT HOLDER

BACKGROUND OF THE INVENTION

1. Field Of the Invention

The present invention relates generally to a holder for dental and medical instruments and, in particular, to an instrument holder which allows for easy sterilization of the instrument and holder between uses.

2. Description of the Prior Art

Instrument holders have been used in the fields of medicine and dentistry for many years and are well known to practitioners. These holders provide a location for instruments to be placed and stored when they are not in use. Examples of such holders are taught in U.S. Pat. Nos. 3,904,841 and 4,330,281.

U.S. Pat. No. 3,904,841 is directed to a holder for a powered handpiece which provides means for interrupting the power to the handpiece and also includes a lockout feature for selectively maintaining the interruption of power while the handpiece remains removed from the holder. U.S. Pat. No. 4,330,281 teaches an improved dental handpiece holder which grips the handpiece at the region of the grip portion adjacent to the tailstock portion and is provided with a plurality of supporting surfaces which differ from the conventional holding receptacle for improving the use of the instrument.

While the aforementioned patents may improve the ease of use and accessibility of the instrument, there is an important problem which is not addressed by these, or any other, patents. This problem arises due to the fact that medical and dental instruments become directly, or indirectly, contaminated with blood and other bodily fluids during dental procedures, causing the instrument holder to become contaminated. Thus, if the instrument holder is not properly sterilized between patients, it is possible to transmit serious diseases from one patient to another by way of a contaminated instrument holder. This may happen if a dental instrument is used on an infected patient and is returned to the instrument holder. If the instrument holder becomes contaminated, it may serve as a reservoir of an infectious pathogen. Therefore, if the instrument holder itself is not sufficiently sterilized between patients, any instrument inserted into the holder will be contaminated, even if the instrument itself has been properly sterilized between patient uses, and may infect subsequent patients.

Awareness of these conditions has been heightened recently with reports of HIV transmission in the dental operatory. With the realization that HIV (the virus which causes the deadly AIDS disease) or potentially deadly diseases, including viral hepatitis and tuberculosis, can be transmitted in the dental office, infection control has become an increasingly important issue. If both contaminated instruments and instrument holders are not properly sterilized, diseases may be transmitted from patient to patient in the dental office, with death a possible consequence.

Current instrument holders used in dental offices are not designed to be sterilized between patients. These holders are typically formed as a single unit which is permanently affixed or mounted within the dental operatory using screws, bolts, or adhesives. Thus, there is no efficient manner by which the holders can be removed for proper sterilization.

SUMMARY OF THE INVENTION

It is therefore an object of the present invention to provide a medical instrument holder which can be easily and effectively sterilized between patients to eliminate the possibility of disease transmission resulting from contaminated instrument holders.

It is also an object of the present invention to provide an instrument holder which can easily be removed from a mounting bracket to be conveniently and effectively sterilized.

It is a further object of the present invention to provide an instrument holder which can supply a variety of power sources, such as electricity and/or pneumatics, along with other desired features, such as water and/or vacuum, to a dental instrument.

Still another object of the present invention is to provide an instrument holder which can be economically manufactured, and can be adapted or formed to hold dental instruments of different external configurations, such as handpieces, vacuum tips, air/water syringes and the like.

These and other objects are accomplished in the present instance by a novel instrument holder which is constructed as two easily separable sections. The first section is a mounting bracket which is rigidly affixed to a surface within the operatory. The second section is an instrument holder, capable of temporarily supporting instruments, which separably attaches to the mounting bracket section, allowing it to be easily removed from the bracket without the use of tools and properly sterilized.

DETAILED DESCRIPTION OF THE PREFERRED EMBODIMENT

Figure 1:
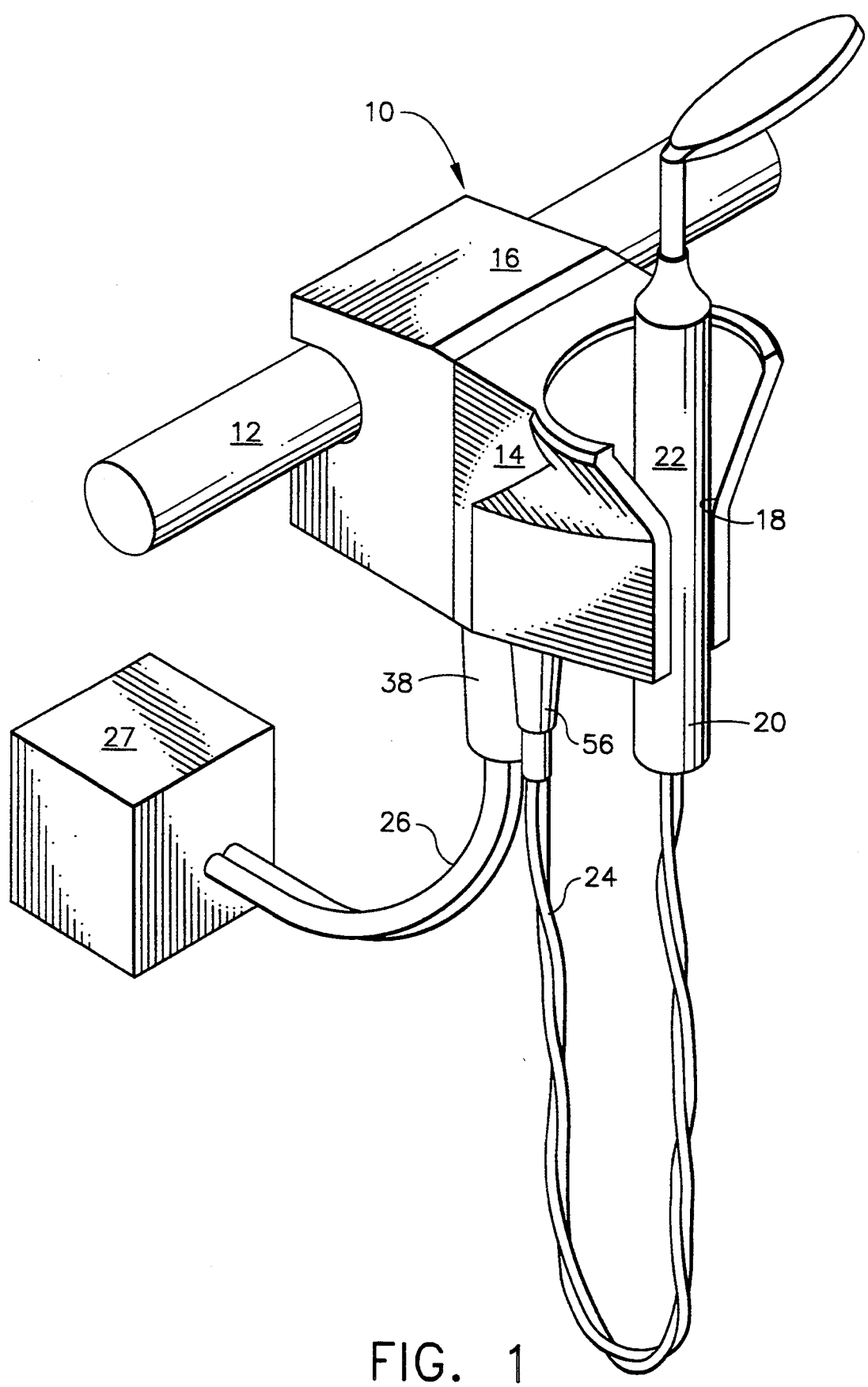
FIG. 1 is a perspective view of a preferred embodiment of a dental instrument with a holder in accordance with the present invention.
Figure 2:
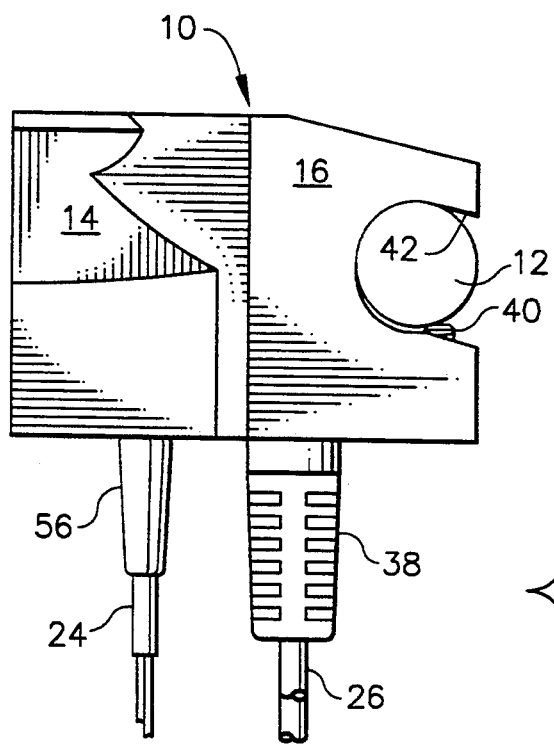
FIG. 2 is a fragmentary side view of the holder assembly shown in FIG. 1.
Figure 3:
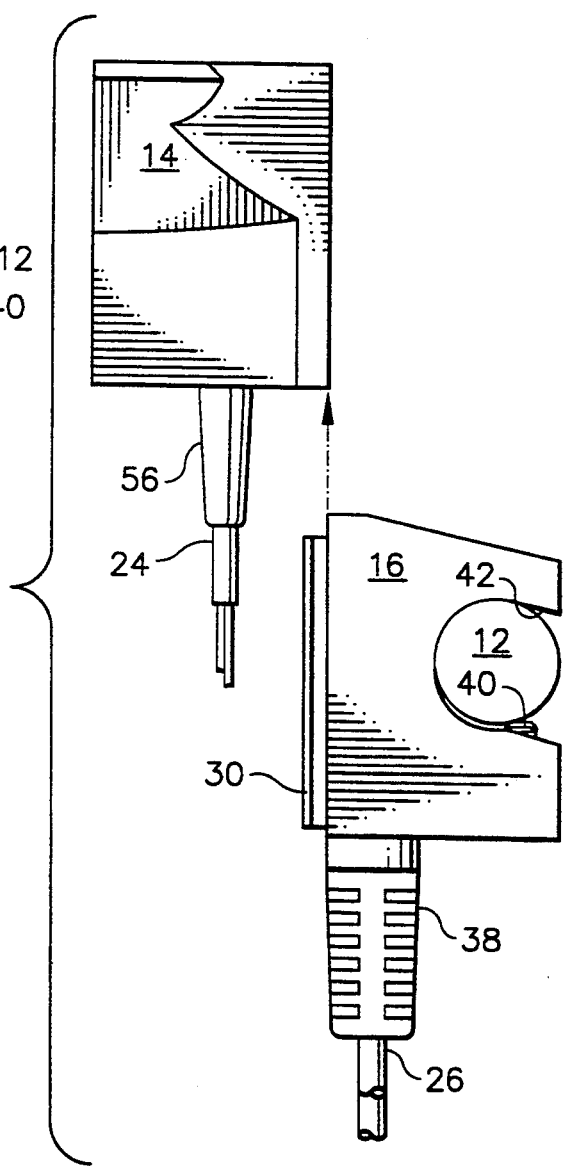
FIG. 3 is a fragmentary side view of the holder assembly shown in FIG. 1 with its two sections separated.
Figure 4:
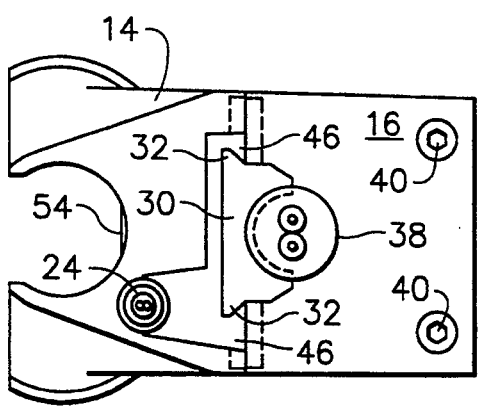
FIG. 4 is a bottom view, partially in cross-section, of the holder assembly of FIG. 2.
Figure 5:
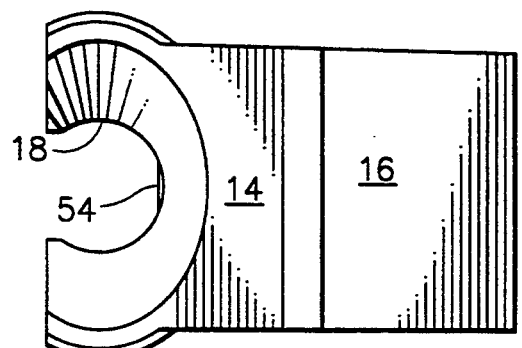
FIG. 5 is a top view of the holder assembly shown in FIG. 2.
Figure 6:
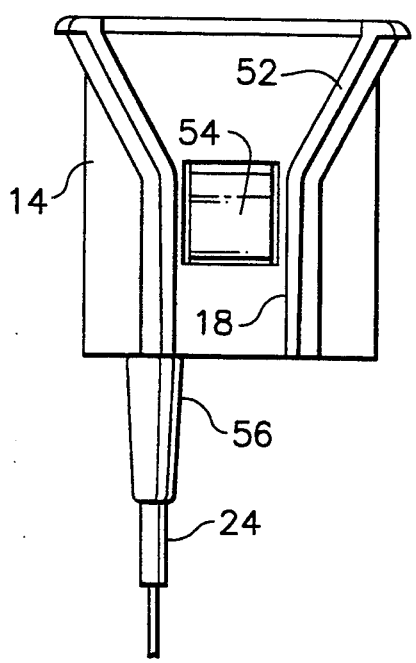
FIG. 6 is a front view of the tool holder section of the assembly shown in FIG. 2.
Figure 7:
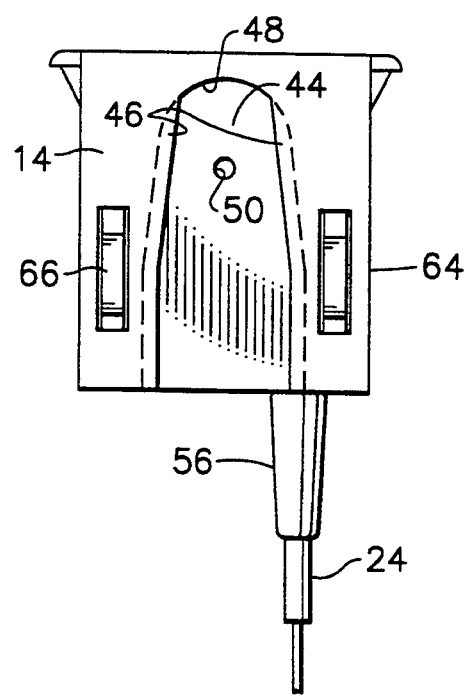
FIG. 7 is a rear view of the tool holder section of the assembly shown in FIG. 2.
Figure 8:
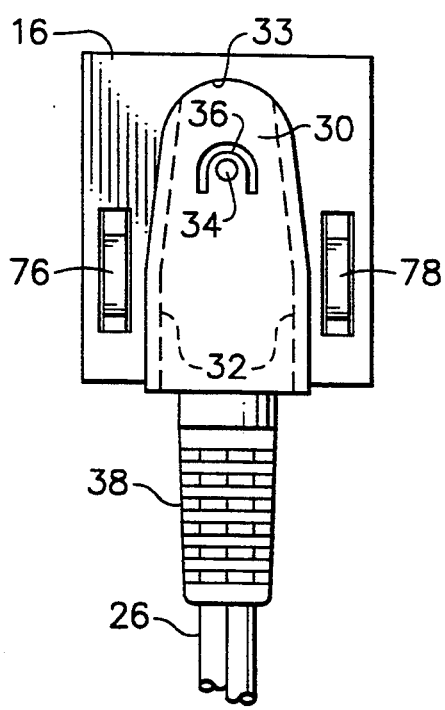
FIG. 8 is a front view of the mounting bracket section of the assembly shown in FIG. 2.
Figure 9:
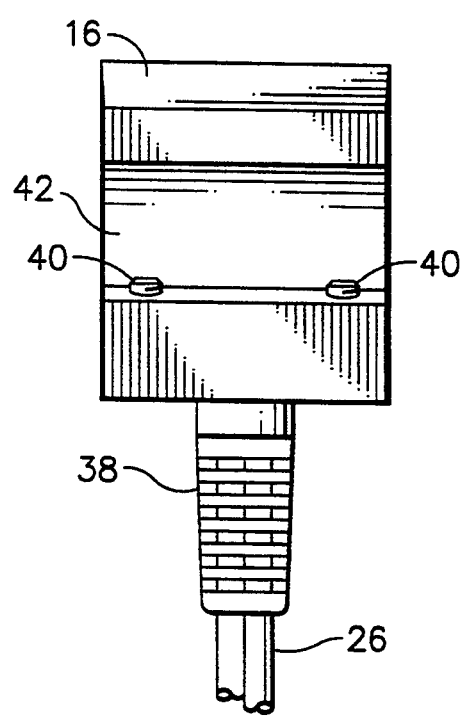
FIG. 9 is a rear view of the mounting bracket section of the assembly shown in FIG. 2.

Referring now to FIG. 1, an instrument holder assembly 10 according to the present invention is shown mounted on a suitable support 12. Assembly 10 consists of an instrument holder section 14 and mounting block section 16. Located along the front of section 14 is a channel 18 for releasably engaging an instrument 20.

Instrument 20 is preferably an instrument similar to that described in the co-pending U.S. patent application Ser. No. 08/089,251 which is assigned to the same assignee as the present application. Instrument 20 contains a handpiece section 22 which is frictionally held within channel 18 of holder section 14. Sections 14 and 16 are preferably constructed of a heat resistant material, such as plastic.

Extending from the bottom of holder section 14 is an electrical cord 24 which is connected at its other end to instrument 20 for providing energy to operate instrument 20. Extending from the bottom of mounting block section 16 is a second electrical cord 26. Cord 26 is connected at its other end to a suitable power source 27 which provides the energy to tool holder assembly 10 necessary for the operation of instrument 20. In the preferred embodiment, power source 27 is electricity, but it would also be compressed air, vacuum, water or the like.

The structure of assembly 10 can more clearly be seen in FIGS. 2-9. Mounting block section 16 contains an extended surface or flange 30 having V shaped edges 32 along either side which converge along a rounded portion 33. Also located on flange 30 is a lug 34. Lug 34 is located on a flexible tongue 36 of flange 30 such that lug 34 is capable of movement. At the bottom end of mounting block section 16, a cord grip 38 holds cord 26 in its proper location within section 16. Finally, a plurality of set screws 40 extend from the bottom end of section 16 into a cylindrical channel 42 along the rear side of section 16. Support 12 is held firmly in position within channel 42 by applying tension to screws until support 12 is firmly engaged by screws 40.

Instrument holder section 14 contains a cutaway section 44 having the same dimensions as flange 30 on mounting block section 16. Section 44 contains a V shaped channel 46 along each side, and terminates in a rounded portion 48. The central portion of section 44 also contains a round aperture 50 corresponding to lug 34 of flange 30 of section 16.

Channel 18 of instrument holder section 14 terminates in a flared portion 52 toward the top end of section 14. In addition, an electrical switch contact 54 is located within channel 18. Finally, a cord grip 56 located on the edge of section 14 holds cord 24 from instrument 20 in its proper location within section 14. The sides of channel 18 may be constructed of a flexible material so that instruments of varying external configurations can be secured within said channel.

Figure 10:
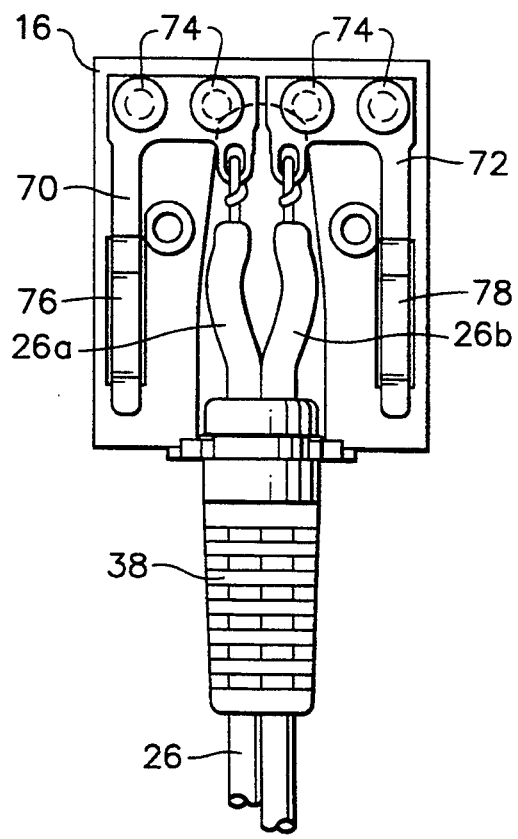
FIG. 10 is a cross-sectional view of the mounting block section shown in FIG. 8.
Figure 11:
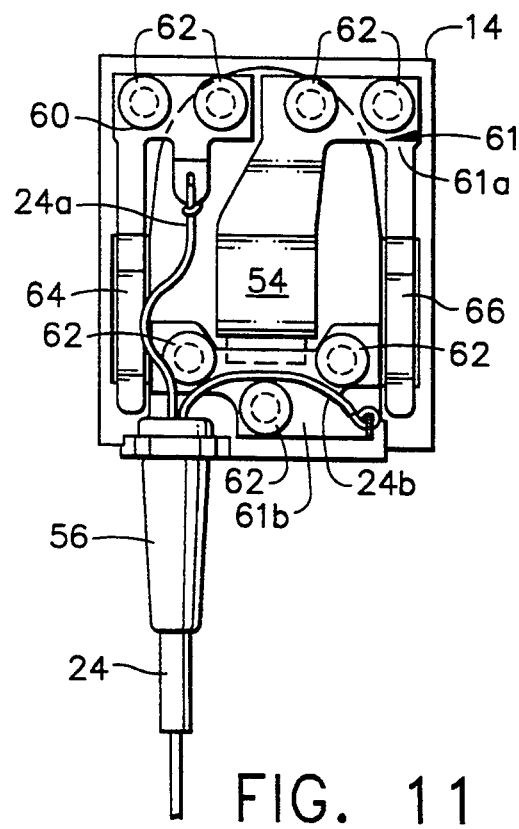
FIG. 11 is a cross-sectional view of the tool holder section shown in FIG. 6.
Figure 12:
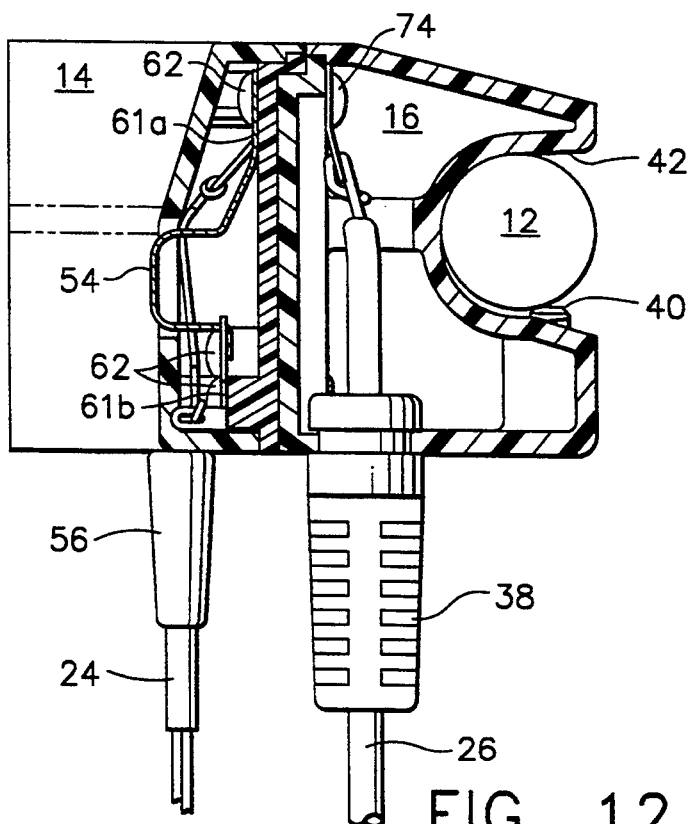
FIG. 12 is a cross-sectional view of the assembly shown in FIG. 2.

The electrical circuitry for operating instrument 20 can most clearly be seen in FIGS. 10 and 11. Referring first to FIG. 11, leads 24a and 24b of cord 24 extend through cord grip 56 into holder section 14, and are connected to a pair of electrical contacts 60 and 61, respectively. Contact 60 is positioned within holder section 14 by a plurality of rivets 62, or any other suitable fastening means which will provide electrical isolation from holder section 14. Contact 61 is comprised of two sections 61a and 61b which are kept in physical contact by switching contact 54 which extends into channel 18, the operation of which will be explained more fully hereinafter. Contact sections 61a and 61b are also fastened to section 14 using a plurality of rivets 62. A section 64 of contact 60 extends from holder section 14, while a section 66 of contact 61 also extends from holder section 14 on the opposite side of cutaway section 44, as can be more dearly seen in FIG. 7.

Referring now to FIG. 10, leads 26a and 26b of cord 26 extend through cord grip 38 into mounting block section 16, and are connected to a pair of electrical contacts 70 and 72, respectively. Contacts 70 and 72 are individually fastened to section 16 using a plurality of rivets 74. Contact 70 contains a section 76 extending from block section 16, and contact 72 similarly contains a section 78 extending from block section 16 on the opposite side of flange 30, as can be more clearly seen in FIG. 8.

The operation of tool holder assembly 10 and instrument 20 will now be described. Mounting block section 18 is first secured to a solid surface, such as a ½ inch bar, which is the standard mounting in the dental office. The mounting surface is placed within channel 42 of mounting block section 18 and set screws 40 are tightened until section 18 is secured tightly in the desired position. Tool holder section 14 is now secured to section 18 by sliding flange 30 of section 18 into mating cutaway section 44 of holder 14. V shaped edges 32 of section 16 cooperate with V shaped channel 46 of section 14 to secure the sections of assembly 10 together. Lug 34 of tongue 36 on flange 30 fits into aperture 50 in cutaway section 44, and holds sections 14 and 16 together tightly with the action of flexible tongue 36. Cord 26 is then connected to a suitable power source.

The electrical contacts 76 and 78 of section 16 are in physical contact with contacts 66 and 64 of section 14 when the two sections are secured together, thus providing energy to operate instrument 20.

When instrument 20 is placed within channel 18 of tool holder section 14, as shown in FIG. 1, switching contact 54 is forced away from section 61b of contact 61, breaking the electrical circuit and putting instrument 20 in the off condition. When it is desired to use instrument 20, handpiece section 22 is grasped and physically removed from channel 18. As instrument 20 is removed, switching contact 54 shifts to a position in contact with section 61b, allowing current to flow through cord 26 to instrument 20, enabling instrument 20 to operate. After use of instrument has been completed, tool holder section 14 can be easily separated from mounting block section 18 by pushing on the bottom of section 14 until the force is sufficient to move lug 34 out of aperture 50, and channel 46 of section 14 is moved out of mating contact with flange 30 of section 16. When sections 14 and 16 of tool holder assembly 10 have been separated, instrument 20 and instrument holder section 14, which are connected by cord 24, can be sterilized as a unit by any conventional sterilizing means.

In the above description, and in the claims which follow, the use of such words as "up", "down", "forward", "rearward", "vertical", "horizontal", and the like, is in conjunction with the drawings for purposes of clarity. As will be understood by one skilled in the art, the device can assume any orientation during use, depending upon the application to which it is directed.

While the present invention has been shown and described in terms of preferred embodiments thereof, it will be understood that this invention is not limited to any particular embodiment and that many changes and modifications may be made without departing from the true spirit and scope of the invention as defined in the appended claims. For example, the two sections of assembly 10 could be coupled together by use of a set of female receptacles on one section and a corresponding set of male pins on the other section, by a mating tongue and groove arrangement on the respective sections or using a magnetic arrangement to hold the sections together. In addition, a combination of power sources, such as compressed air, water, and/or vacuum could be provided through the instrument holder assembly of the present invention to an instrument, using well known and commonly available techniques and devices, such as switches or quick-disconnect couplings.

What is claimed is:

1. A holder assembly for a powered instrument, comprising:
    a first section for rigidly affixing the assembly to a support, said first section containing means for connecting said first section to a power supply; and
    a second section, releasably coupled to said first section, for releasably holding a powered instrument, said second section containing means for supplying power to said instrument;
    whereby when said first and second sections are coupled together, energy from the power supply is transferred via said first and second sections to the instrument for operating the instrument, and when said first and second sections are separated, said second section containing said instrument holding means is disconnected from the power supply, and may be sterilized.

2. The assembly of claim 1, wherein said second section includes means for selectively supplying energy from the power supply to the instrument.

3. The assembly of claim 2, wherein said selection means is activated when an instrument is held by said releasably holding means so as to interrupt energy to said instrument.

4. The assembly of claim 1, wherein said first section is affixed to the support by the use of screws.

5. The assembly of claim 1, wherein the means for releasably holding the instrument comprises a flexible support capable of holding instruments of varying external configurations.

6. A holder assembly for a powered instrument capable of being sterilized, comprising:
    an instrument capable of operation by a power supply;
    an instrument holding section, having means for releasably supporting said instrument, and power supplying means coupling said holding section to said instrument; and
    a supporting section, releasably coupled to said holding section, for rigidly affixing the assembly to a base, having means for coupling the assembly to a power supply,
    whereby said instrument holding section and said instrument can be removed from said supporting section for sterilization purposes.

7. The assembly of claim 6, wherein said instrument holding section includes a flange and said supporting section includes a channel corresponding to said flange such that said flange cooperates with said channel to releasably couple said support section to said holding section.

8. A holder assembly for a powered instrument, comprising:
    a first section for affixing the assembly to a support, said first section containing means for coupling said first section to at least one power supply; and a second section, releasably coupled to said first section, for holding a powered instrument, said second section containing means for supplying power from said at least one power supply to said instrument;
    whereby when said first and second sections are coupled together, energy from said power supply is transferred via said first and second sections to the instrument, and when said first and second sections are separated, said second section containing said instrument holding means is disconnected from said power supply, and may be sterilized.

9. The assembly of claim 8, wherein said at least one power supply provides electrical energy for the instrument.

10. The assembly of claim 8, wherein said at least one power supply provides a vacuum for the instrument.

11. The assembly of claim 8, wherein said at least one power supply provides water for the instrument.

12. The assembly of claim 8, wherein a plurality of power supplies provide both electricity and vacuum to the instrument.

13. The assembly of claim 8, wherein a plurality of power supplies provide both electricity and compressed air to the instrument.

14. The assembly of claim 8, wherein said second section contains means for disconnecting the instrument from said power supply.

15. The assembly of claim 8, wherein said at least one power supply provides compressed air for the instrument.

* * * * *